United States Patent [19]

Drewes et al.

[11] Patent Number: 5,288,776
[45] Date of Patent: Feb. 22, 1994

[54] SUBSTITUTED PYRROLES AS STABILISERS FOR CHLORINATED POLYMERS

[75] Inventors: Rolf Drewes, Lindenfels; Hans-Helmut Friedrich, Lautertal, both of Fed. Rep. of Germany

[73] Assignee: Ciba-Geigy Corporation, Ardsley, N.Y.

[21] Appl. No.: 709,690

[22] Filed: Jun. 3, 1991

[30] Foreign Application Priority Data

Jun. 7, 1990 [CH] Switzerland ............... 1907/90-7

[51] Int. Cl.$^5$ ............... C08K 5/3415; C07D 207/00; C07D 295/00
[52] U.S. Cl. ............... 524/94; 548/539; 548/540; 548/560
[58] Field of Search ............... 524/94; 548/539, 540, 548/560

[56] References Cited

U.S. PATENT DOCUMENTS 3,551,571 12/1970 Pachter et al. .
3,644,631 2/1972 Pachter et al. .
4,369,276 1/1983 Wirth et al. .

FOREIGN PATENT DOCUMENTS 0419792 4/1991 European Pat. Off. .
2078761 1/1982 United Kingdom .

OTHER PUBLICATIONS

Chemical Abstracts 84:121713c 1976.
Chemical Abstracts 96:19906d 1981.
Chemical Abstracts 87:39211r 1977.
Chemical Abstracts 84:105327z 1975.
Chemical Abstracts 112:198025j 1989.
Angel Alberola, et al., Heterocycles, vol. 29, No. 10, 1989, pp. 1973–1982.
L. G. Tikhonova, et al., Zh. Org. Khim., 11,2510 (1975).
H. A. Houwing, et al., Tetrahedron Lett., 2, 143 (1976).
P. F. dos Santos Filho et al, Angew. Chem., 89, 672 (1977).
H. A. Houwing et al., J. Heterocycl. Chem., 18, 1127 (1981).
Chemical Abstracts 115:209373m.

*Primary Examiner*—Kriellion S. Morgan
*Attorney, Agent, or Firm*—Luther A. R. Hall; W. A. Teoli, Jr.

[57] ABSTRACT

A composition comprising
a) a chlorinated polymer, and
b) at least one compound of formula I

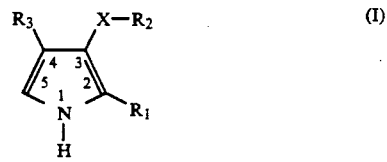

wherein X is a group

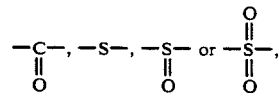

$R_1$ and $R_2$ are each independently of the other $C_1$–$C_{20}$alkyl, hydroxy- and/or halogen-substituted $C_1$–$C_{10}$alkyl, $C_3$–$C_{20}$alkenyl, $C_5$–$C_{12}$cycloalkyl, $C_1$–$C_4$alkyl-substituted $C_5$–$C_8$cycloalkyl, phenyl or phenyl which is substituted by 1 to 3 radicals $A_1$, which radicals $A_1$ are each independently of one another selected from the group consisting of $C_1$–$C_{10}$alkyl, halogen, hydroxy, methoxy and ethoxy, $R_1$ and $R_2$ are further $C_7$–$C_{10}$phenylalkyl or $C_7$–$C_{10}$phenylalkyl which is substituted in the phenyl moiety by 1 to 3 radicals $A_2$, which radicals $A_2$ are each independently of one another selected from the group consisting of $C_1$–$C_{20}$alkyl, halogen, hydroxy, methoxy and ethoxy, and $R_3$ is phenyl or phenyl which is substituted by 1 to 3 radicals $A_3$, which radicals $A_3$ are each independently of one another selected from the group consisting of $C_1$–$C_{10}$alkyl, halogen, hydroxy, methoxy, ethoxy and ($C_1$–$C_8$alkyl)oxycarbonyl, with the proviso that at least one of the radicals $R_1$ and $R_2$ is phenyl or substituted phenyl as defined above and $R_1$ is different from methyl if $R_2$ is phenyl.

Some of the compounds of formula I are novel.

13 Claims, No Drawings

SUBSTITUTED PYRROLES AS STABILISERS FOR CHLORINATED POLYMERS

The present invention relates to chlorinated polymers containing substituted pyrroles, to the use of said pyrroles for stabilising chlorinated polymers against heat- and light-induced degradation, and to novel pyrroles.

It is known that chlorinated polymers need to be protected against the harmful effect of light and heat, especially when processing them to moulded articles. The use of pyrroles as stabilisers for chlorinated thermoplastics is disclosed, for example, in U.S. Pat. No. 4,369,276 and GB-A-2 078 761.

The preparation of substituted pyrroles is disclosed, for example, in the following publications: L. G. Tikhonova et al.; Zhurnal Organicheskoi Khimii 11, 2510-14 (1975), H. A. Houwing et al.; Tetrahedron Letters 2, 143-6 (1976), P. F. dos Santos Filho et al.; Angew. Chem. 89, 672-3 (1977) and H. A. Houwing et al.; J. Heterocycl. Chem. 18, 1127-32 (1981).

The use of pyrroles as medicaments is disclosed in BE-A-715 405.

The present invention relates to compositions comprising
a) a chlorinated polymer, and
b) at least one compound of formula I

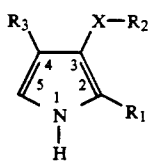

wherein X is a group

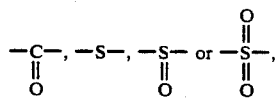

$R_1$ and $R_2$ are each independently of the other $C_1$-$C_{20}$alkyl, hydroxy- and/or halogen-substituted $C_1$-$C_{10}$alkyl, $C_3$-$C_{20}$alkenyl, $C_5$-$C_{12}$cycloalkyl, $C_1$-$C_4$alkyl-substituted $C_5$-$C_8$cycloalkyl, phenyl or phenyl which is substituted by 1 to 3 radicals $A_1$, which radicals $A_1$ are each independently of one another selected from the group consisting of $C_1$-$C_{10}$alkyl, halogen, hydroxy, methoxy and ethoxy, $R_1$ and $R_2$ are further $C_7$-$C_{10}$phenylalkyl or $C_7$-$C_{10}$phenylalkyl which is substituted in the phenyl moiety by 1 to 3 radicals $A_2$, which radicals $A_2$ are each independently of one another selected from the group consisting of $C_1$-$C_{20}$alkyl, halogen, hydroxy, methoxy and ethoxy, and $R_3$ is phenyl or phenyl which is substituted by 1 to 3 radicals $A_3$, which radicals $A_3$ are each independently of one another selected from the group consisting of $C_1$-$C_{10}$alkyl, halogen, hydroxy, methoxy, ethoxy and ($C_1$-$C_8$alkyl)oxycarbonyl, with the proviso that at least one of the radicals $R_1$ and $R_2$ is phenyl or substituted phenyl as defined above and $R_1$ is different from methyl if $R_2$ is phenyl.

The compounds of formula I have a very good stabilising action not only against heat-induced, but also against light-induced, degradation. The long-term stabilising efficiency is especially remarkable.

Preferably $R_1$ is different from $C_1$-$C_3$alkyl, especially $C_1$-$C_{20}$alkyl, if $R_2$ is phenyl.

Halogen is preferably chloro.

Alkyl of up to 20 carbon atoms is typically methyl, ethyl, propyl, butyl, tert-butyl, pentyl, hexyl, heptyl, octyl, isooctyl, isononyl, decyl, dodecyl or octadecyl.

Hydroxy- and/or halogen-substituted $C_1$-$C_{10}$alkyl is conveniently 5-hydroxypentyl, 2,3,5-trihydroxypentyl or 5-chloropentyl.

$C_3$-$C_{20}$Alkenyl is typically allyl, 2-methallyl, 3-methylbut-2-enyl, 3-methylbut-3-enyl, hexenyl, decenyl, undecenyl, heptadecenyl or oleyl. Preferred meanings are allyl, methallyl and oleyl.

$C_5$-$C_{12}$Cycloalkyl is typically cyclopentyl, cyclohexyl, cycloheptyl, cyclooctyl, cyclodecyl or cyclododecyl. The preferred meaning is $C_5$-$C_7$cycloalkyl, more particularly cyclohexyl.

$C_1$-$C_4$alkyl-substituted, preferably methyl-substituted, $C_5$-$C_8$cycloalkyl is typically methylcyclohexyl or tert-butylcyclohexyl.

Phenyl which is substituted by 1 to 3 radicals as defined above is typically o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 2-methyl-4-tert-butylphenyl, 2-ethylphenyl, 2,6-diethylphenyl, 2,6-diethyl-4-methylphenyl, 2,6-diisopropylphenyl, 4-tert-butylphenyl, p-nonylphenyl, o-, m- or p-chlorophenyl, 2,3-dichlorophenyl, 2,4-dichlorophenyl, 2,5-dichlorophenyl, 2,6-dichlorophenyl, 3,4-dichlorophenyl, 2,4,5-trichlorophenyl, 2,4,6-trichlorophenyl, o-, m- or p-hydroxyphenyl, o-, m- or p-methoxyphenyl, o- or p-ethoxyphenyl, 2,4-dimethoxyphenyl, 2,5-dimethoxyphenyl, 2,5-diethoxyphenyl, o-, m- or p-methoxycarbonyl, 2-chloro-6-methylphenyl, 3-chloro-2-methylphenyl, 3-chloro-4-methylphenyl, 4-chloro-2-methylphenyl, 5-chloro-2-methylphenyl, 2,6-dichloro-3-methylphenyl, 2-hydroxy-4-methylphenyl, 3-hydroxy-4-methylphenyl, 2-methoxy-5-methylphenyl, 4-methoxy-2-methylphenyl, 3-chloro-4-methoxyphenyl, 3-chloro-6-methoxyphenyl, 3-chloro-4,6-dimethoxyphenyl and 4-chloro-2,5-dimethoxyphenyl.

$C_7$-$C_{10}$Phenylalkyl is conveniently benzyl or 2-phenylethyl. Benzyl is preferred. If the phenyl group in these radicals is substituted by 1 to 3 groups, it may have the meanings given hereinabove. $C_7$-$C_{10}$Phenylalkyl which is substituted in the phenyl moiety by $C_1$-$C_{20}$alkyl, preferably by $C_8$-$C_{14}$alkyl, is one of the preferred meanings. A further example is dodecylbenzyl.

Interesting compositions are those wherein $R_1$ und $R_2$ are each independently of the other $C_1$-$C_{20}$alkyl, hydroxy-substituted $C_1$-$C_5$alkyl, $C_3$-$C_{17}$alkenyl, $C_5$-$C_7$cycloalkyl, $C_1$-$C_4$alkyl-substituted $C_5$-$C_7$cycloalkyl, phenyl, phenyl which is substituted by 1 to 3 radicals $A_1$, $C_7$-$C_{10}$phenylalkyl or $C_7$-$C_{10}$phenylalkyl which is substituted in the phenyl moiety by 1 to 3 radicals $A_2$, and $R_3$ is phenyl or phenyl which is substituted by 1 to 3 radicals $A_3$.

Preferred compositions are also those in which $R_1$ and $R_2$ are each independently of the other $C_1$-$C_{17}$alkyl, hydroxy-substituted $C_1$-$C_5$alkyl, $C_3$-$C_{17}$alkenyl, cyclohexyl, $C_1$-$C_4$alkyl-substituted cyclohexyl, phenyl or phenyl which is substituted by 1 to 3 radicals $A_1$, which radicals $A_1$ are each independently of one another $C_1$-$C_4$alkyl, chloro, hydroxy, methoxy or ethoxy, $R_1$ and $R_2$ are also benzyl or benzyl which is substituted in the phenyl nucleus by 1 to 3 radicals $A_2$, which radicals $A_2$ are each independently of one another $C_8$–$C_{14}$alkyl, chloro, hydroxy, methoxy or ethoxy, and $R_3$ is phenyl or phenyl which is substituted by 1 to 3 radicals $A_3$, which radicals $A_3$ are each independently of one another $C_1$–$C_4$alkyl, chloro, hydroxy, methoxy or ethoxy.

Also preferred are compositions wherein $R_1$ und $R_2$ are each independently of the other $C_1$–$C_{17}$alkyl, hydroxy-substituted $C_1$–$C_5$alkyl or phenyl, and $R_3$ is phenyl or phenyl which is substituted by a radical $A_3$, which radical $A_3$ is $C_1$–$C_4$alkyl, chloro or methoxy.

The radical $R_1$ is preferably phenyl.

Particularly preferred compositions are those wherein $R_1$ and $R_3$ are phenyl and $R_2$ is phenyl or $C_4$–$C_{17}$alkyl.

The radical X is preferably a group

or -S-, most preferably

Preferred examples of compounds of formula I are 2,4-diphenyl-3-benzoylpyrrole and 2,4-diphenyl-3-octadecanoylpyrrole.

The chlorinated polymers are preferably vinyl chloride homopolymers or copolymers. Suitable comonomers for the copolymers are typically: vinyl acetate, vinylidene chloride, transdichloroethane, ethylene, propylene, butylene, maleic acid, acrylic acid, fumaric acid, itaconic acid. Further suitable chlorinated polymers are postchlorinated PVC and chlorinated polyolefins, and also graft polymers of PVC with EVA, ABS and MBS. Preferred substrates are also mixtures of the aforementioned homopolymers and copolymers, especially vinyl chloride/homopolymers with other thermoplastic and/or elastomeric polymers, preferably with ABS, MBS, NBR, SAN and EVA.

Other preferred polymers are suspension and mass polymers as well as emulsion polymers.

The most preferred chlorinated polymer is polyvinyl chloride.

The compounds of formula I may be used together with known heat stabilisers, such as organotin compounds, lead compounds, organic antimony compounds, Me(II) phenolates, preferably $C_7$–$C_{20}$alkylphenolates, typically nonyl phenolate, or Me(II) carboxylates. Me(II) denotes conveniently Ba, Ca, Mg, Cd or Zn. The carboxylates are preferably salts of carboxylic acids of 7 to 20 carbon atoms, typically benzoates, alkenoates or alkanoates, preferably stearates, oleates, laurates, palmitates, hydroxystearates or 2-ethylhexanoates. Especially preferred carboxylates are stearates, oleates and p-tert-butylbenzoates. Illustrative examples of organotin compounds, lead compounds and organic antimony compounds are the compounds listed in U.S. Pat. No. 4,743,640 column 3, line 48 to column 5, line 38.

In addition, the chlorinated polymers stabilised with the compounds of formula I may contain conventional PVC stabilisers, such as phosphites or epoxy compounds, in customary amounts.

The phosphites are preferably those of formulae

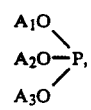

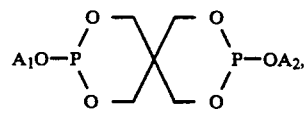

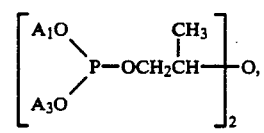

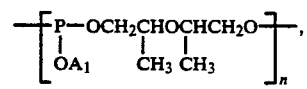

wherein $A_1$, $A_2$ and $A_3$ are each independently of one another $C_4$–$C_{18}$alkyl, $C_6$–$C_{18}$alkenyl, $C_5$–$C_7$cycloalkyl, phenyl or phenyl which is substituted by one to three $C_1$–$C_{12}$alkyl groups.

Representative examples of such phosphites are trioctyl, tridecyl, tridodecyl, tritetradecyl, tristearyl, trioleyl, triphenyl, tricresyl, tris(p-nonylphenyl) and tricyclohexyl phosphite. Preferred phosphites are the aryldialkylphosphites as well as the alkyldiaryl phosphites, for example phenyldidecyl phosphite, (2,4-di-tert-butylphenyl)didodecyl phosphite, (2,6-di-tert-butylphenyl)didodecyl phosphite and the dialkyl and diaryl pentaerythritol diphosphites, such as distearyl pentaerythritol diphosphite. Also preferred are the tetraphenyl- and tetraalkyl-[1,2-dipropylene glycol] diphosphites and the poly[1,2-dipropylene glycol phenylphosphites] as well as the poly[1,2-dipropylene glycol alkylphosphites].

Particularly preferred organic phosphites are distearyl pentaerythritol diphosphite, tris(nonylphenyl)phosphite, phenyldidecyl phosphite, tetraphenyl-[1,2-dipropylene glycol] diphosphite and poly[1,2-dipropylene glycol phenylphosphite].

The epoxy compounds are preferably epoxidised oils and epoxidised fatty acid esters, for example epoxidised soybean oil, epoxidised butyl oleate and epoxidised octyl oleate.

The invention hence preferably relates also to compositions comprising, in addition to component a) and a compound of formula I, at least one Me(II) carboxylate and/or Me(II) phenolate, where Me(II) is Ba, Ca, Mg, Cd or Zn.

In a further preferred embodiment of the invention, the novel compositions comprise, in addition to component a) and a compound of formula I, at least one Me(II) carboxylate, where Me(II) is Ba, Ca, Mg or Zn. Mixtures of barium/zinc carboxylates or calcium/zinc carboxylates are especially preferred co-stabilisers.

Preferred compositions are also those comprising, in addition to component a) and a compound of formula I, an epoxy compound and/or a phosphite and optionally an Me(II) carboxylate and/or Me(II) phenolate.

The material to be stabilised may contain the known heat stabilisers (for example carboxylates) in a concentration known to the skilled person, typically in an amount of 0.05 to 5% by weight.

The phosphites are added in concentrations of 0.3 to 5% by weight, preferably of 0.5 to 1% by weight, and the epoxy compounds, such as epoxidised soybean oil, are conveniently added in concentrations of 1 to 8% by weight, preferably of 1 to 3% by weight.

The compounds of formula I are incorporated in the chlorinated polymer in amounts of typically 0.05 to 5% by weight, preferably 0.05 to 3% by weight and, most preferably, 0.1 to 2.0% by weight.

The percentage by weight amounts refer in each case to the material to be stabilised.

Depending on the end use requirements of the polymers, other additives such as phenolic antioxidants, lubricants (preferably montan waxes or glycerol esters), fatty acid esters, paraffins, plasticisers, fillers, carbon black, asbestos, kaolin, talcum, glass fibres, modifiers (such as impact resistance additives), fluorescent whitening agents, pigments, light stabilisers, UV absorbers, flame retardants or antistatic agents, may be incorporated prior to or during incorporation of the stabilisers.

Other possible additives are $\beta$-aminocrotonates, for example the compounds disclosed in DE-A-804 442, DE-A-807 207 and JP-A-75/17454, pyrroles, for example the compounds disclosed in EP-A-22 087, aminouracils, for example the compounds disclosed in EP-A-65 934, aminothiouracils, for example the compounds disclosed EP-A-41 479, polyols, for example the compounds disclosed in DE-A-3 019 910, $\beta$-diketones, for example the compounds disclosed in DE-A-2 600 516, or also mixtures of $\beta$-diketones and hydrotalcites as disclosed, for example, in EP-A-63 180.

Further preferred compositions are those comprising, in addition to component a) and a compound of formula I, a $\beta$-diketone, such as phenyleicosane-1,3-dione, and optionally a Me(II)carboxylate and/or Me(II) phenolate.

The incorporation of the stabiliser components in the chlorinated polymer is best effected in conventional manner on a two-roll mill in the temperature range from 150° C. to 200° C. A sufficiently homogeneous mixture is normally obtained within 5 to 15 minutes. The addition of the components can be made individually or together as a premix. A liquid premix has proved useful, i.e. processing is carried out in the presence of inert solvents and/or plasticizers.

The compositions of the invention can be processed to moulded articles by the conventional shaping techniques, typically by extrusion, injection moulding or calendaring. The use as plastisols is also possible, The compositions of the invention are preferably used for making electrical cables, hollow bodies such as tubes, and, in particular, sheets for the automotive industry. This utility is likewise an object of the invention. A particularly preferred field of use is making sheets for motor vehicle interiors, especially as described in DE-A 3 227 107 and DE-A 3 401 482.

The compositions of the invention are used with particular advantage for making PVC-based deep-drawn sheets and flexible sheets, especially for use in the automotive industry.

The invention further relates to the use of the compounds of formula I for stabilising chlorinated polymers against heat- and light-induced degradation.

The invention still further relates to the novel compounds of formula Ib

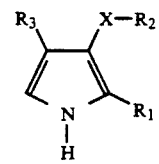

wherein X is a group

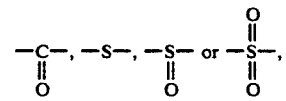

$R_1$ and $R_2$ are each independently of the other $C_1$–$C_{20}$alkyl, halogen-substituted $C_1$–$C_{10}$alkyl, $C_3$–$C_{20}$alkenyl, $C_5$–$C_{12}$cycloalkyl, $C_1$–$C_4$alkyl-substituted $C_5$–$C_8$cycloalkyl, phenyl or phenyl which is substituted by 1 to 3 radicals $A_1$, which radicals $A_1$ are each independently of one another selected from the group consisting of $C_1$–$C_{10}$alkyl, halogen, hydroxy, methoxy and ethoxy, $R_1$ and $R_2$ are further $C_7$–$C_{10}$phenylalkyl which is substituted in the phenyl moiety by 1 to 3 radicals $A_2$, which radicals $A_2$ are each independently of one another selected from the group consisting of $C_1$–$C_{20}$alkyl, halogen, hydroxy, methoxy and ethoxy, and $R_3$ is phenyl or phenyl which is substituted by 1 to 3 radicals $A_3$, which radicals $A_3$ are each independently of one another selected from the group consisting of $C_1$–$C_{10}$alkyl, halogen, hydroxy, methoxy, ethoxy and ($C_1$–$C_8$alkyl)oxycarbonyl, with the proviso that at least one of the radicals $R_1$ and $R_2$ is phenyl or substituted phenyl as defined above and $R_1$ is different from methyl and phenyl if $R_2$ is phenyl.

Preferred meanings of the substituents X, $R_1$, $R_2$ and $R_3$ are those as indicated above for formula I.

The compounds of formula I can be prepared by methods analogous to known ones, for example Knorr's pyrrole synthesis or as described by P. F. dos Santos Filho et al. in Angew. Chem. 89, 672 (1977), in accordance with the following reaction scheme.

Scheme A:

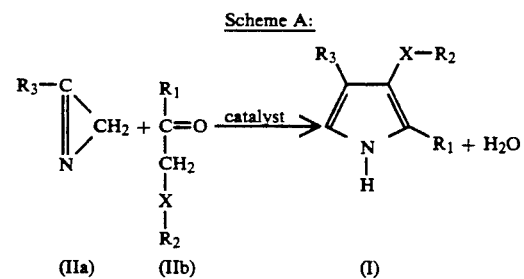

The reaction is preferably carried out in a polar aprotic organic solvent such as acetone, in the temperature range from conveniently 10° to 80° C., preferably from 30° to 50° C. A suitable catalyst is conveniently a transition metal compound, preferably nickel acetylacetonate.

The compounds of formula I can be obtained in the synthesis as a mixture. This mixture contains, in addition to the compounds of formula I, compounds of formula Ia

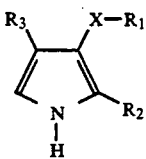

wherein the molar ratio of compounds of formula I to compounds of formula Ia is conveniently 1:4 to 4:1. If necessary, this mixture can be separated by crystallisation or by means of chromatographic methods.

Accordingly, the invention also relates to compositions comprising
a) a chlorinated polymer, and
b) a mixture of compounds of formulae I and Ia,

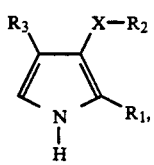

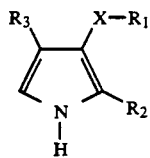

wherein X, $R_1$, $R_2$ and $R_3$ are as defined above.

Most of the compounds of formulae IIa and IIb are commercially available, but they can also be obtained by methods analogous to known ones (for example: S. Padmanabhan et al.; Bull. Chem. Soc. Jpn. 62, 1358-1360 (1989); N. Kunieda et al.; Bull. Chem. Soc. Jpn. 54, 1143 (1981)).

The invention is illustrated in more detail by the following Examples in which, unless otherwise stated, parts and percentages are by weight.

EXAMPLE 1

Preparation of 2,4-diphenyl-3-benzoylpyrrole

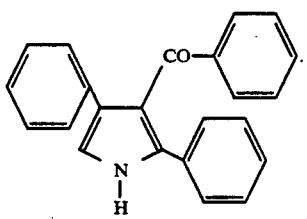

With stirring, 3.0 g of 2-phenylazirine are added dropwise to a solution of 5.6 g of dibenzoylmethane, 10 ml of acetone and 0.1 g of nickel acetylacetonate at 50° C. The mixture is then heated at reflux for 30 minutes, cooled to 20° C., and 25 ml of water are added. The precipitated crystals are filtered with suction, washed with water, and dried to constant weight.

Yield: 7.8 g ($\simeq$96.3% of theory) of yellow crystals.

Melting point: 195°-196° C. (after recrystallisation from isopropanol).

EXAMPLES 2-6

The compounds listed in Table 1 are prepared in accordance with the general procedure described in Example 1.

TABLE 1

| Ex. | Compound | Melting point | Comments |
|---|---|---|---|
| 2 | ![structure] | 237° C. | 2-(p-Methylphenyl)azirine is used as starting material. The reaction product is recrystallised from ethyl acetate/dimethyl formamide. |
| 3 | ![structure] | 204-205° C. | 2-(p-Chlorophenyl)azirine is used as starting material. The reaction product is recrystallised from ethyl acetate. |
| 4 | ![structure] | 90-92° C. | The compounds of Examples 4 and 5 are obtained together as a mixture and can be separated by recrystallisation from petroleum ether. |

TABLE 1-continued

| Ex. | Compound | Melting point | Comments |
|---|---|---|---|
| 5 | 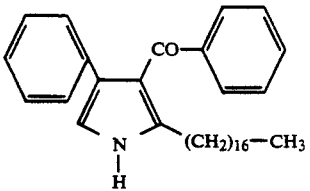 | $n_D^{30} = 1.5433$ | |
| 6 | 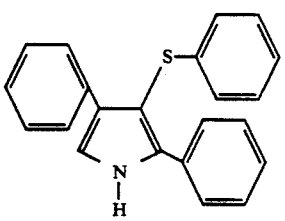 | 128–129° C. | The reaction product is recrystallised from isopropanol/H$_2$O. |

EXAMPLE 7

Preparation of a mixture of 2,4-diphenyl-3-(3'-methylbutanoyl)pyrrole and 2-isobutyl-3-benzoyl-4-phenylpyrrole in the molar ratio 42:48.

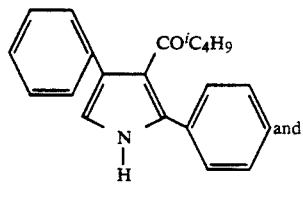

and

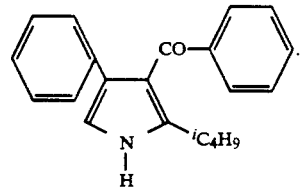

The preparation is carried out in accordance with the general procedure described in Example 1. 1-Phenyl-heptane-1,3-dione and 2-phenylazirine are used as reactants. After recrystallisation from petroleum ether/toluene, the mixture has a melting point of 118°–120° C.

If desired, both components of the mixture can be separated by means of chromatographic methods.

EXAMPLE 8

Preparation of a mixture of 2-(5'-hydroxypentyl)-3-benzoyl-4-phenylpyrrole and 2,4-diphenyl-3-(6'-hydroxyhexanoyl)pyrrole in the molar ratio 1:1

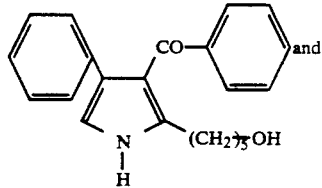

-continued

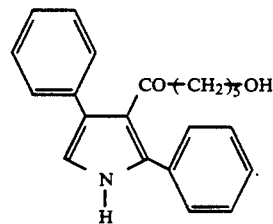

11.7 g of 2-phenylazirine are added dropwise at 25° C. (cooling with a water bath) to 30 ml of acetone, 23.4 g of 1-phenyl-8-hydroxyoctane-1,3-dione and 0.1 g of nickel acetylacetonate. To bring the reaction to completion, the mixture is heated for 30 minutes at reflux. After cooling, the reaction mixture is dissolved in 150 ml of diethyl ether, washed with water and sodium hydrogencarbonate, dried, and concentrated to dryness on a rotary evaporator.

Yield: 20.5 g ($\simeq$ 61.6% of theory) of a brown resin.

NMR spectrum: Several multiplets with together 10H: 1.0–3.6 ppm. O-H: 2.0–2.3 ppm. Two doublets (together 1H): 6.6 and 6.7 ppm. Multiplet, 10H: 6.9–7.7 ppm.

If desired, both components of the mixture can be separated by means of chromatographic methods.

EXAMPLE 9

Preparation of a mixture of 2-phenyl-3-octadecanoyl-4-p-chlorophenylpyrrole and 2-heptadecyl-3-benzoyl-4-p-chlorophenylpyrrole in the molar ratio 2:3.

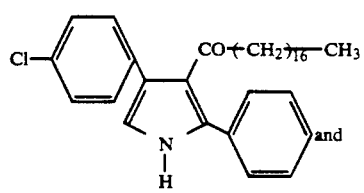

and

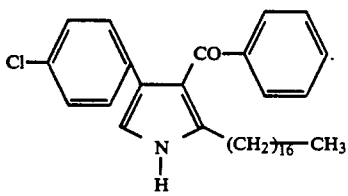

11.4 g of p-chlorophenylazirine are added dropwise at 20° C. to a solution of 60 ml of acetone, 0.2 g of nickel acetylacetonate and 32.5 g of 1-phenyleicosane-1,3-dione and heated for 30 minutes at reflux. The solvent is distilled off on a rotary evaporator and the residue is recrystallised from 500 ml of acetonitrile. The crystals are filtered with suction and dried.

Yield: 33.0 g ($\simeq$85% of theory) of white crystals. Melting point: 58°–76° C.

If desired, both components of the mixture can be separated by means of chromatographic methods.

EXAMPLE 10

Preparation of 2-phenyl-3-octadecanoyl-4-p-chlorophenylpyrrole.

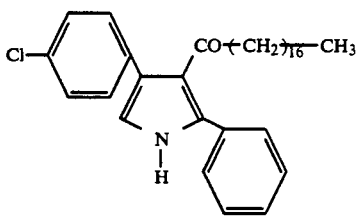

The mother liquor obtained in the synthesis of Example 9 is cooled to 0° C. and the precipitated crystals are isolated.

Yield: 6.0 g ($\simeq$15% of theory) of white crystals. Melting point: 46°–50° C.

EXAMPLE 11

Preparation of a mixture of 2-phenyl-3-octadecanoyl-4-p-methylphenylpyrrole and 2-heptadecyl-3-benzoyl-4-p-methylphenylpyrrole in the molar ratio 45:55

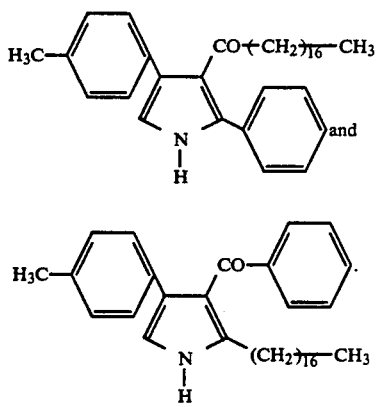

The preparation is carried out in accordance with the general procedure described in Example 9. The reactants are 2-p-methylphenylazirine and 1-phenyleicosane-1,3-dione. The resultant product is recrystallised from 300 ml of acetonitrile. The crystals are isolated and dried.

Yield: 22.3 g ($\simeq$60% of theory) of yellow crystals. Melting point: 100°–113° C.

If desired, both components of the mixture can be separated by means of chromatographic methods.

EXAMPLE 12

Preparation of 2-phenyl-3-octadecanoyl-4-p-methylphenylpyrrole

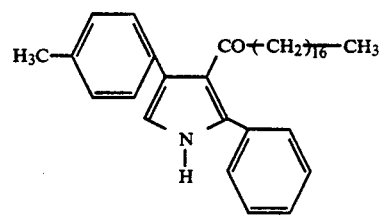

The mother liquor obtained in the synthesis of Example 11 is cooled to 0° C. and the precipitated crystals are isolated.

Yield: 8.1 g ($\simeq$21.6% of theory) of pale yellow crystals. Melting point: 46°–48° C.

EXAMPLE 13

Preparation of a mixture of 2,4-diphenyl-3-acetylpyrrole and 2-methyl-3-benzoyl-4-phenylpyrrole in the molar ratio 55:45.

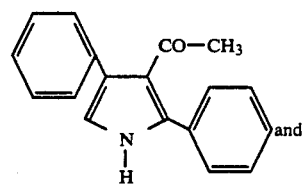

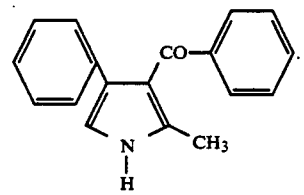

The preparation is carried out in accordance with the general procedure described in Example 1. The reactants are 2-phenylazirine and benzoylacetone.

Yield: 97% of theory.

Melting point: 196°–205° C.

If desired, both components of the mixture can be separated by means of chromatographic methods.

EXAMPLE 14

Preparation of 2-ethyl-3-benzoyl-4-phenylpyrrole

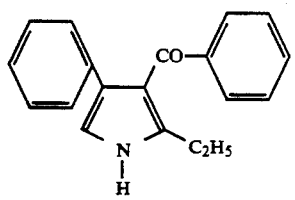

The preparation is carried out in accordance with the general procedure in Example 1. The reactants are 2-phenylazirine and 1-phenylpentane-1,3-dione. The reaction product is dissolved in 150 ml of hot ethanol and the solution is allowed to stand overnight at room temperature. The precipitated crystals are filtered with suction.

Melting point: 175°–178° C.

EXAMPLE 15

Preparation of 2,4-diphenyl-3-propanoylpyrrole

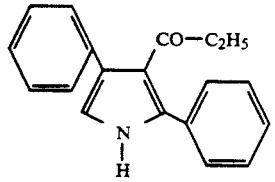

The ethanolic mother liquor obtained according to Example 14 is cooled and the precipitate is filtered with suction.

Melting point: 135°–145° C.

EXAMPLE 16

Preparation of 2-phenyl-3-benzoyl-4-p-methoxyphenylpyrrole

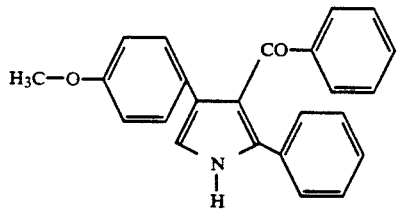

The preparation is carried out in accordance with the general procedure in Example 1. The reactants are dibenzoyl methane and 2-(p-methoxyphenyl)azirine.

Melting point: 161°–163° C.

EXAMPLE 17

Heat test

A dry mixture comprising 100 parts of PVC (K value 60), 5 parts of epoxidised soybean oil, 0.2 part of polyethylene wax, 0.8 part of phenyl-diisodecyl phosphite and 1 part of the stabiliser indicated in Tables 2a to 2c is rolled on a mixer roller for 5 minutes at 180° C. Samples of the 0.3 mm rough sheet so obtained are subjected to heat in a test oven (®Mathis-Thermotester Typ LFT-ST) at 180° C. The time taken until the sample decomposes (decomposition time) is recorded. The results are reported in Tables 2a to 2c. Lengthy decomposition times denote good stabilisation of the polymer.

TABLE 2a

| Stabilizer | Decomposition time in minutes |
|---|---|
| compound of Example 2 | 130 |
| mixture of Example 9 | 135 |

TABLE 2b

| Stabilizer | Decomposition time in minutes |
|---|---|
| compound of Example 1 | 135 |

TABLE 2c

| Stabilizer | Decomposition time in minutes |
|---|---|
| compound of Example 16 | >135 |

EXAMPLE 18

Exposure Test

A dry mixture comprising 100 parts of PVC (K value 60), 5 parts of epoxidised soybean oil, 0.2 part of polyethylene wax, 0.8 part of phenyl-diisodecyl phosphite, 0.02 part of zinc stearate and 1 part of the stabiliser indicated in Example 1 is rolled on a mixer roller for 5 minutes at 180° C. Samples of the 0.3 mm rough sheet so obtained are irradiated with an ®OSRAM ULTRA-VITALUX lamp (300 Watt) at a distance of 50 cm (average exposure temperature: ca. 65° C.). The samples are irradiated at 24 hour intervals, exposure for 8 of the 24 hour cycle being carried out under a ca. 2 cm layer of water and for the remaining 16 hours under dry conditions.

The Yellowness Index (YI) according to ASTM 1925 of a sample is determined at the given interval. The results are reported in Table 3.

TABLE 3

| Exposure in hours | 0 | 8 | 24 | 48 | 72 |
|---|---|---|---|---|---|
| YI | 16.4 | 30.1 | 54.1 | 69.9 | 96.7 |

EXAMPLE 19

Heat Test

A dry mixture comprising 100 parts of PVC, 5 parts of epoxidised soybean oil, 0.35 part of calcium stearate, 0.15 part of zinc stearate, 0.2 part of phenyleicosane-1,3-dione, 15 parts of dioctyl phthalate, 0.1 part of 2-hydroxy-4-methoxybenzophenone and 0.3 part of the stabiliser indicated in Table 4 is rolled on a mixer roller for 5 minutes at 180° C. Samples of the 0.3 mm rough sheet so obtained are subjected to heat in a test oven (®Mathis-Thermotester Typ LFT-ST) at 180° C. The time taken until the sample decomposes (decomposition time) is recorded.

The results are reported in Table 4. Lengthy decomposition times denote good stabilisation of the polymer.

TABLE 4

| Stabilizer | Decomposition time in minutes |
|---|---|
| compound of Example 1 | >140 |
| compound of Example 4 | 120 |

What is claimed is:

1. A composition comprising
a) a chlorinated polymer, and
b) a compound of formula I

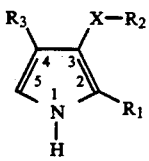

wherein X is a group

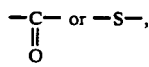

$R_1$ and $R_2$ are each independently of the other $C_1-C_{20}$alkyl, hydroxy- and/or halogen-substituted $C_1-C_{10}$alkyl, $C_3-C_{20}$alkenyl, $C_5-C_{12}$cycloalkyl, $C_1-C_4$alkyl-substituted $C_5-C_8$cycloalkyl, phenyl or phenyl which is substituted by 1 to 3 radicals $A_1$, which radicals $A_1$ are each independently of one another selected from the group consisting of $C_1-C_{10}$alkyl, halogen, hydroxy, methoxy and ethoxy, $R_1$ and $R_2$ are further $C_7-C_{10}$phenylalkyl or $C_7-C_{10}$phenylalkyl which is substituted in the phenyl moiety by 1 to 3 radicals $A_2$, which radicals $A_2$ are each independently of one another selected from the group consisting of $C_1-C_{20}$alkyl, halogen, hydroxy, methoxy and ethoxy, and $R_3$ is phenyl or phenyl which is substituted by 1 to 3 radicals $A_3$, which radicals $A_3$ are each independently of one another selected from the group consisting of $C_1-C_{10}$alkyl, halogen, hydroxy, methoxy, ethoxy and ($C_1-C_8$alkyl)oxycarbonyl, with the proviso that at least one of the radicals $R_1$ and $R_2$ is phenyl or substituted phenyl as defined above and $R_1$ is different from methyl if $R_2$ is phenyl.

2. A compound of formula Ib

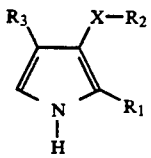

wherein X is a group

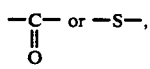

$R_1$ and $R_2$ are each independently of the other $C_1-C_{20}$alkyl, halogen-substituted $C_1-C_{10}$alkyl, $C_3-C_{20}$alkenyl, $C_5-C_{12}$cycloalkyl, $C_1-C_4$alkyl-substituted $C_5-C_8$cycloalkyl, phenyl or phenyl which is substituted by 1 to 3 radicals $A_1$, which radicals $A_1$ are each independently of one another selected from the group consisting of $C_1-C_{10}$alkyl, halogen, hydroxy, methoxy and ethoxy, $R_1$ and $R_2$ are further $C_7-C_{10}$phenylalkyl or $C_7-C_{10}$phenylalkyl which is substituted in the phenyl moiety by 1 to 3 radicals $A_2$, which radicals $A_2$ are each independently of one another selected from the group consisting of $C_1-C_{20}$alkyl, halogen, hydroxy, methoxy and ethoxy, and $R_3$ is phenyl or phenyl which is substituted by 1 to 3 radicals $A_3$, which radicals $A_3$ are each independently of one another selected from the group consisting of $C_1-C_{10}$alkyl, halogen, hydroxy, methoxy, ethoxy and ($C_1-C_8$alkyl)oxycarbonyl, with the proviso that at least one of the radicals $R_1$ and $R_2$ is phenyl or substituted phenyl as defined above and $R_1$ is different from methyl and phenyl if $R_2$ is phenyl, and the compounds 3-(p-methoxy)benzoyl-2-methyl-4-phenylpyrrole and 3-acetyl-2,4-diphenylpyrrole are disclaimed.

3. A composition according to claim 1, wherein $R_1$ und $R_2$ are each independently of the other $C_1-C_{20}$alkyl, hydroxy-substituted $C_1-C_5$alkyl, $C_3-C_{17}$alkenyl, $C_5-C_7$cycloalkyl, $C_1-C_4$alkyl-substituted $C_5-C_7$cycloalkyl, phenyl, phenyl which is substituted by 1 to 3 radicals $A_1$, $C_7-C_{10}$phenylalkyl or $C_7-C_{10}$phenylalkyl which is substituted in the phenyl moiety by 1 to 3 radicals $A_2$, and $R_3$ is phenyl or phenyl which is substituted by 1 to 3 radicals $A_3$.

4. A composition according to claim 1, wherein $R_1$ and $R_2$ are each independently of the other $C_1-C_{17}$alkyl, hydroxy-substituted $C_1-C_5$alkyl, $C_3-C_{17}$alkenyl, cyclohexyl, $C_1-C_4$alkyl-substituted cyclohexyl, phenyl or phenyl which is substituted by 1 to 3 radicals $A_1$, which radicals $A_1$ are each independently of one another $C_1-C_4$alkyl, chloro, hydroxy, methoxy or ethoxy, $R_1$ and $R_2$ are also benzyl or benzyl which is substituted in the phenyl nucleus by 1 to 3 radicals $A_2$, which radicals $A_2$ are each independently of one another $C_8-C_{14}$alkyl, chloro, hydroxy, methoxy or ethoxy, and $R_3$ is phenyl or phenyl which is substituted by 1 to 3 radicals $A_3$, which radicals $A_3$ are each independently of one another $C_1-C_4$alkyl, chloro, hydroxy, methoxy or ethoxy.

5. A composition according to claim 1, wherein $R_1$ and $R_2$ are each independently of the other $C_1-C_{17}$alkyl, hydroxy-substituted $C_1-C_5$alkyl or phenyl, and $R_3$ is phenyl or phenyl which is substituted by a radical $A_3$, which radical $A_3$ is $C_1-C_4$alkyl, chloro or methoxy.

6. A composition according to claim 1, wherein $R_1$ is phenyl.

7. A composition according to claim 1, wherein $R_1$ and $R_3$ are phenyl and $R_2$ is phenyl or $C_4-C_{17}$alkyl.

8. A composition according to claim 1, wherein component b) is a mixture of compounds of formulae I and Ia

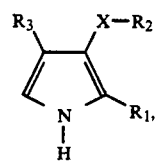

-continued

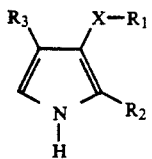
(Ia)

wherein X, $R_1$, $R_2$ and $R_3$ are as defined in claim 1.

9. A composition according to claim 1, wherein the chlorinated polymer is polyvinyl chloride.

10. A composition according to claim 1, which additionally comprises a Me(II) carboxylate and/or Me(II) phenolate, where Me(II) denotes Ba, Ca, Mg, Cd or Zn.

11. A composition according to claim 1, which additionally comprises a Me(II) carboxylate and/or Me(II) phenolate, where Me(II) denotes Ba, Ca, Mg, Cd or Zn, and/or a β-diketone.

12. A composition according to claim 1, which additionally comprises an epoxy compound and/or a phosphite.

13. A process for stabilising a chlorinated polymer against heat- and light-induced degradation, which comprises incorporating in said chlorinated polymer a compound of formula I as defined in claim 1.

* * * * *